US009457192B2

(12) United States Patent
Birkholz et al.

(10) Patent No.: US 9,457,192 B2
(45) Date of Patent: *Oct. 4, 2016

(54) SYSTEMS AND METHODS FOR MONITORING NEUROSTIMULATION DOSING

(71) Applicant: Cardiac Pacemakers, Inc., St. Paul, MN (US)

(72) Inventors: Doug M. Birkholz, Shoreview, MN (US); Douglas J. Brandner, New Brighton, MN (US); Douglas J. Gifford, Ham Lake, MN (US); David J. Ternes, Roseville, MN (US); William J. Linder, Golden Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/612,799

(22) Filed: Feb. 3, 2015

(65) Prior Publication Data

US 2015/0148867 A1 May 28, 2015

Related U.S. Application Data

(63) Continuation of application No. 13/780,903, filed on Feb. 28, 2013, now Pat. No. 8,965,521.

(60) Provisional application No. 61/612,833, filed on Mar. 19, 2012.

(51) Int. Cl.
*A61N 1/375* (2006.01)
*A61N 1/372* (2006.01)
(Continued)

(52) U.S. Cl.
CPC ............ *A61N 1/3727* (2013.01); *A61N 1/3605* (2013.01); *A61N 1/36082* (2013.01); *A61N 1/36125* (2013.01); *A61N 1/36142* (2013.01); *A61N 1/36178* (2013.01); *A61N 1/378* (2013.01)

(58) Field of Classification Search
CPC .......... A61N 1/36125; A61N 1/3605; A61N 1/36082; A61N 1/36178; A61N 1/36142; A61N 1/3727; A61N 1/378
USPC ...................................... 607/59, 45
See application file for complete search history.

(56) References Cited

U.S. PATENT DOCUMENTS 4,074,720 A 2/1978 Malchman et al.
6,014,587 A * 1/2000 Shaw ................. A61N 1/08
607/45

(Continued)

OTHER PUBLICATIONS

U.S. Appl. No. 13/780,903, Corrected Notice of Allowance mailed Jan. 28, 2015, 2 pgs.

(Continued)

*Primary Examiner* — Edward Moran
*Assistant Examiner* — Michael Carey
(74) *Attorney, Agent, or Firm* — Schwegman Lundberg & Woessner, P.A.

(57) ABSTRACT

Various implantable device embodiments may comprise a neural stimulator configured to deliver a neurostimulation therapy with stimulation ON times and stimulation OFF times where a dose of the neurostimulation therapy is provided by a number of neurostimulation pulses over a period of time. The neural stimulator may be configured to monitor the dose of the delivered neurostimulation therapy against dosing parameters. The neural stimulator may be configured to declare a fault if the monitored dose does not favorably compare to a desired dose for the neurostimulation therapy, or may be configured to record data for the monitored dose of the delivered neurostimulation therapy, or may be configured to both record data fir the monitored dose of the delivered neurostimulation therapy and declare a fault if the monitored dose does not favorably compare to a desired dose for the neurostimulation therapy.

18 Claims, 13 Drawing Sheets

(51) Int. Cl.
*A61N 1/36* (2006.01)
*A61N 1/378* (2006.01)

(56) References Cited

U.S. PATENT DOCUMENTS

| | | |
|---|---|---|
| 7,751,884 B2 | 7/2010 | Ternes et al. |
| 7,826,897 B2 | 11/2010 | Stubbs et al. |
| 8,055,343 B2 | 11/2011 | Gandhi et al. |
| 8,214,164 B2 | 7/2012 | Gandhi et al. |
| 8,352,029 B2 | 1/2013 | Ternes et al. |
| 8,364,261 B2 | 1/2013 | Stubbs et al. |
| 8,965,521 B2 * | 2/2015 | Birkholz ............ A61N 1/36125 607/45 |
| 2005/0275382 A1 | 12/2005 | Stessman et al. |
| 2008/0097544 A1 | 4/2008 | Gandhi et al. |
| 2009/0182517 A1 * | 7/2009 | Gandhi ................ A61N 1/3708 702/58 |
| 2010/0234912 A1 | 9/2010 | Ternes et al. |
| 2011/0046689 A1 | 2/2011 | Stubbs et al. |
| 2011/0313488 A1 | 12/2011 | Ordonez et al. |
| 2013/0245718 A1 | 9/2013 | Birkholz et al. |

OTHER PUBLICATIONS

U.S. Appl. No. 13/780,903, Non Final Office Action mailed Jun. 18, 2014, 15 pgs.

U.S. Appl. No. 13/780,903, Notice of Allowance mailed Oct. 9, 2014, 7 pgs.

U.S. Appl. No. 13/780,903, Response filed Aug. 26, 2014 to Non Final Office Action mailed Jun. 18, 2014, 16 pgs.

* cited by examiner

NORMAL OPERATION

SYSTEMS AND METHODS FOR MONITORING NEUROSTIMULATION DOSING

CLAIM OF PRIORITY

This application is a continuation of U.S. application Ser. No. 13/780,903, filed Feb. 28, 2013, now issued as U.S. Pat. No. 8,965,521, which claims the benefit of priority under 35 U.S.C. §119(e) of U.S. Provisional Patent Application Ser. No. 61/612,833, entitled "SYSTEMS AND METHODS FOR MONITORING NEURO STIMULATION DOSING," filed on Mar. 19, 2012, each of which is herein incorporated by reference in its entirety.

TECHNICAL FIELD

This application relates generally to medical devices and, more particularly, to neurostimulation systems, devices and methods.

BACKGROUND

Neurostimulation has been proposed as a therapy for respiratory problems such as sleep disordered breathing, blood pressure control such as to treat hypertension, cardiac rhythm management, myocardial infarction and ischemia, heart failure, epilepsy, depression, pain, migraines, eating disorders, obesity, inflammatory diseases, and movement disorders. Neurostimulation may be delivered acutely for acute conditions or may be delivered more chronically tier chronic conditions. Furthermore, neurostimulation may be delivered to a variety of neural targets, such as peripheral neural targets, spinal neural targets, motor nerve targets and autonomic nerve targets.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscles around blood vessels, for example. The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing," The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent neurons convey impulses towards the central nervous system (CNS), and efferent neurons convey impulses away from the CNS.

SUMMARY

Various embodiments provide a method that may include delivering a neurostimulation therapy where a dose of the neurostimulation therapy is provided by a number of neurostimulation pulses over a period of time. The method may include monitoring the dose of the delivered neurostimulation therapy. The method may further include declaring a fault if the monitored dose does not favorably compare to a desired dose or recording data for the monitored dose of the delivered neurostimulation therapy.

Various implantable device embodiments may comprise a neural stimulator configured to deliver a neurostimulation therapy with stimulation ON times and stimulation OFF times where a dose of the neurostimulation therapy is provided by a number of neurostimulation pulses over a period of time. The neural stimulator may be configured to monitor the dose of the delivered neurostimulation therapy against dosing parameters. The neural stimulator may be configured to declare a fault if the monitored dose does not favorably compare to a desired dose for the neurostimulation therapy or record data for the monitored dose of the delivered neurostimulation therapy.

For example, some embodiments may declare a fault without recording data for the monitored dose, some embodiments may record data for the monitored dose without declaring a fault, and some embodiments may both declare a fault and record data for the monitored dose. Declaring faults may be used to provide safety controls for the neurostimulation, and recording data may be used to document compliance with a prescribed dose of neurostimulation.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
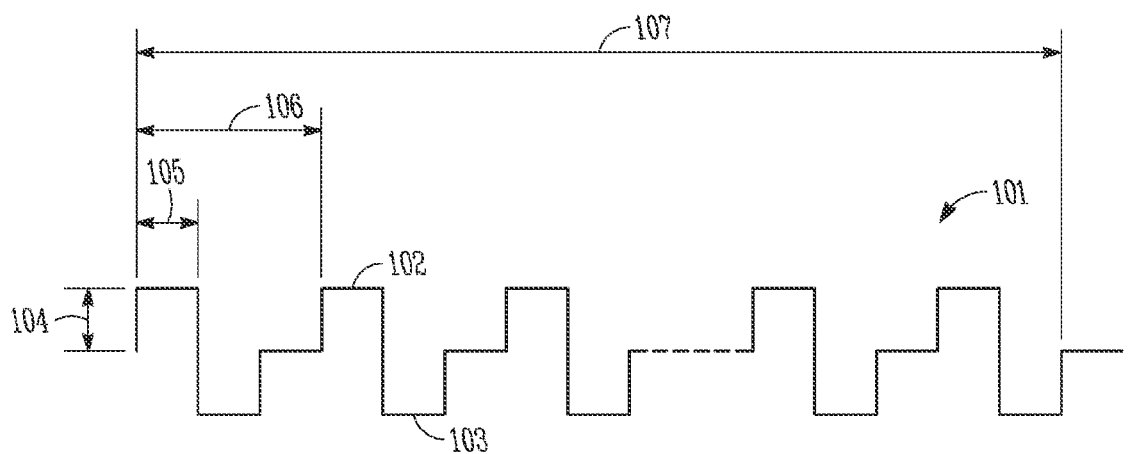
FIG. 1 illustrates, by way of example, biphasic current waveform.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

This document refers to neurostimulation dose, which can relate to an amount of charge delivered to the stimulated tissue. A neurostimulation dose can be an indicator for neurostimulation safety or an indicator for the therapeutic amount of the neurostimulation. In addition to the amount of charge, the neurostimulation dose may also involve a time component, such that the dose may refer to the amount of charge delivered to the stimulated tissue over a period of time. If all other stimulation parameters stay the same, the amount of charge delivered, and the dose of the delivered neurostimulation, increases if a pulse frequency is increased, or a pulse amplitude is increased, or a pulse width is increased, or a duration of burst of stimulation pulses is increased, or a duty cycle is increased for bursts of neurostimulation. Various embodiments of the present subject matter monitor the neurostimulation dosing, which may be used in verifying that a desired neurostimulation dose is being delivered to the patient and/or may be used in providing controls to limit neurostimulation dosing to safe levels.

Nerve recruitment, effectiveness and neural safety depend on charge delivered and charge density (current amp×pulse width/electrode area). U.S. application Ser. No. 13/55,549, filed Jun. 8, 2011 and entitled "Automatic Neurostimulation Titration Sweep" discusses neurostimulation safety and is incorporated herein by reference in its entirety. For example, the threshold current is reduced as the pulse width of the stimulation pulse increases. For example, prolonged neurostimulation, such as may be delivered to treat chronic conditions as has been proposed for some autonomic modulation therapy (AMT), may exceed the charge injection time and may cause damage in the peripheral/central nervous system. Neural damage might occur if a device delivers stimulation that exceeds a charge injection limit for the neural tissue. Generally, more demyelination of the nerve occurs when neurostimulation is delivered at higher pulse frequencies or if the duration of the stimulation increases. Demyelination can possibly differ between different nerve and nerve fiber types. Delivering neurostimulation using intermittent neurostimulation with a duty cycle may eliminate or reduced demyelination. Some techniques that may be used to deliver neurostimulation include current-controlled stimulation, which can control the amount of charge delivered since it is not dependent on the varying tissue-electrode impedance. Additionally, biphasic charge-balanced pulsatile waveforms may be used to deliver neurostimulation therapies to avoid net direct current, which may cause damage to the neural tissue.

This document refers to neurostimulation, and further refers to AMT as an example of neurostimulation. AMT has been used to generally refer to neurostimulation of a neural target in the autonomic nervous system. A reduction in parasympathetic nerve activity contributes to the development and progression of a variety of cardiovascular diseases, and AMT may be implemented to treat such diseases. Neurostimulation to treat cardiovascular diseases may be referred to as neurocardiac therapy (NCT). Vagal stimulation used to treat cardiovascular diseases may be termed either vagal stimulation therapy (VST) or NCT. However, VST may be delivered for non-cardiovascular diseases, and NCT may be delivered by stimulating neural target other than the vagal nerve, such as but not limited to spinal nerves. AMT may but does not necessarily include VST, as AMT may be delivered by stimulating a vagus nerve or by stimulation various other parasympathetic or sympathetic targets in the body, including but not limited to cardiac fats pads, a carotid sinus nerve, a glossopharyngeal nerve, baroreceptor regions, and chemoreceptor regions. Furthermore, AMT may but does not necessarily include NCT. Examples of cardiovascular diseases or conditions that may be treated using VST include hypertension, cardiac remodeling, and heart failure which refers to a clinical syndrome in which cardiac function causes a below normal cardiac output that can fall below a level adequate to meet the metabolic demand of peripheral tissues.

Various embodiments may deliver the neurostimulation intermittently as a programmed series of stimulation ON times separated by stimulation OFF times. Stimulation pulses may be monophasic or biphasic. For example, FIG. 1 illustrates biphasic current waveform 101. A biphasic current waveform has two consecutive pulse phases that have equal charge but opposite polarity and no net DC component. These consecutive pulse phases may be referred to as a stimulating phase 102 that elicits the desired physiological response and a reversal phase 103 that recovers the charge that was delivered during the first phase. FIG. 1 also illustrates the amplitude 104 of the simulating phase, a phase or pulse width 105 of the stimulating phase, the pulse period 106 (1/pulse frequency), and the neurostimulation burst duration 107. The neurostimulation burst comprises a train of neurostimulation pulses.

Figure 2:
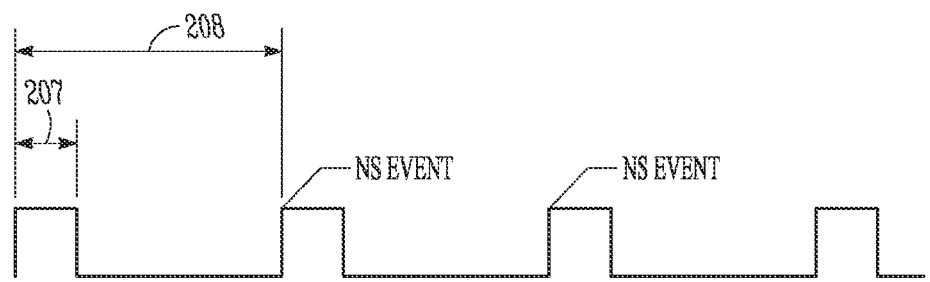
FIG. 2 illustrates, by way of example, a representation of intermittent neurostimulation (INS).

FIG. 2 illustrates a representation of intermittent neurostimulation (INS). The figure diagrammatically shows the time-course of neurostimulation that alternates between intervals of stimulation being ON, when one stimulation pulse or a set of grouped stimulation pulses (i.e., a burst 207) is delivered, and intervals of stimulation being OFF, when no stimulation pulses are delivered. Thus, for example, some embodiments may deliver a plurality of pulses such as the biphasic pulses illustrated in FIG. 1 within a neurostimulation burst illustrated in FIG. 2. The duration of the stimulation ON interval is sometimes referred to as the stimulation duration or burst duration. The start of a stimulation ON interval is a temporal reference point NS Event. The time interval between successive NS Events is the INS Interval, which is may be referred to as the stimulation period or burst period 208. For an application of neurostimulation to be intermittent, the stimulation duration (i.e., ON interval) must be less than the stimulation period (i.e., INS Interval) when the neurostimulation is being applied. The duration of the ON interval relative to the INS Interval (e.g., expressed as a ratio) is sometimes referred to as the duty cycle of the INS. The charge delivered to the neural tissue over a period of time using the waveform illustrated in FIGS. 1 and 2, and thus the neurostimulation dose, depends on the amplitude 104, the pulse width 105, the pulse period 106, the burst duration 107 and 207, and the burst period 208.

Various embodiments of the present subject matter monitor neurostimulation dosing. Some embodiments may monitor the dosing for excessive neurostimulation pulses, and implement one or more safety controls to limit the delivered neurostimulation. For example, the safety control(s) may protect against demyelination that may be caused by an excessive burst duration 107 and 207, by an excessive pulse frequency (e.g. too small of a pulse period 106), by an inadequate time between successive neurostimulation bursts, or by too many neurostimulation pulses over a defined period of time. Some embodiments may monitor the delivered dose for compliance with a prescribed dose, and may record data pertaining to delivered dose. For example, the data for the delivered dose may be recorded in computer-readable memory or discrepancies from the prescribed does may be recorded in computer-readable memory.

Figure 3:
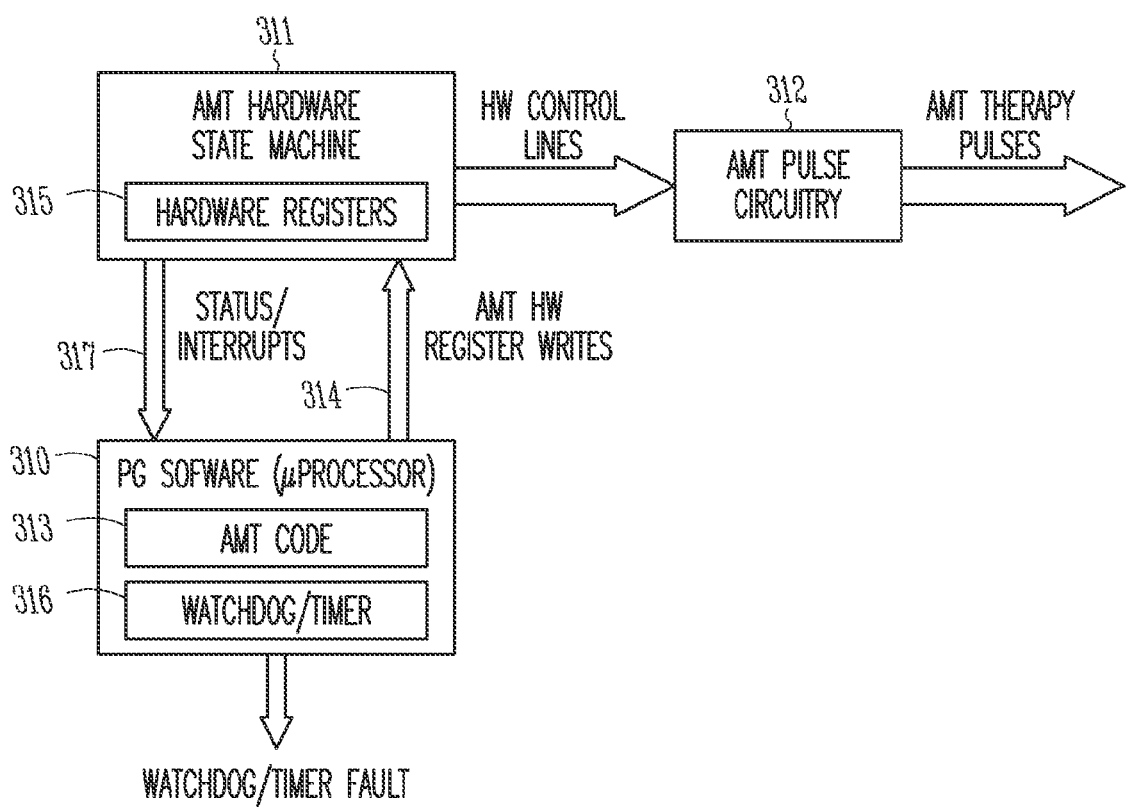
FIG. 3 illustrates, by way of example, an embodiment of a neural stimulator configured to monitor neurostimulation burst starts and/or stops.

FIG. 3 illustrates, by way of example, an embodiment of a neural stimulator configured to monitor neurostimulation burst starts and/or stops. The illustrated neural stimulator 309 includes a processor 310, a hardware state machine 311, and pulse circuitry 312. The processor, such as a microprocessor, is configured to operate on software, including pulse generator (PG) software used to control the delivery of the neurostimulation pulses. The PG software includes code 313 that provides instructions for delivering AMT, for example, or other neurostimulation therapy. The processor may use the AMT code 313 to write data 314 into hardware registers 315 for use by the hardware state machine 311 to control the pulse circuitry 312 to output a train of pulses for the AMT.

The neural stimulator 309 may also operate on firmware instructions. For example, processor 310 may operate on firmware instructions to provide watchdog timer functions 316 that may be used to monitor the delivered dose of the neurostimulation. The monitoring provided by watchdog timer(s) may be used to verify that the delivered dose is within prescribed dosing constraints for the AMT, and/or may be used to limit the AMT if the delivered dose is in excess of the prescribed dosing constraints. The prescribed dosing constraints may include a maximum amount of time that a burst of pulses may be delivered (e.g. Max Burst Stimulation ON), or may include a minimum amount of time without pulses between successive neurostimulation bursts (e.g. Min Burst Stimulation OFF), or may include an allowed relationship between the maximum burst time and the minimum (e.g. ratio of Burst Stimulation ON/(Burst Stimulation OFF+Burst Stimulation ON) or other ratios or relationships). In some embodiments, the watchdog function may be performed by a counter rather than or in addition to a timer. For example, firmware operated on by the processor may count the number of pulses during a Burst Stimulation ON time and compare the count to constraints on the number of pulses that can be delivered within a burst. In some embodiments, the firmware operated on by the processor counts the number of pulses delivered while implementing Stimulation ON and/or Stimulation OFF watchdog timers, and thus may monitor dosing for both excessive pulse frequency and stimulation burst duty cycle.

In some embodiments, the hardware state machine 311 issues interrupts and/or status information 317 to firmware operating in the microprocessor 310. For example, the state machine may issue a Burst Start Interrupt when the first pulse in a burst of neurostimulation pulses is delivered, may issue a Burst Stop Interrupt when the last pulse in a burst of neurostimulation pulses is delivered, or may issue both Burst Start and Burst Stop Interrupts.

Watchdog timer or timers 316 may monitor the delivery of the neurostimulation burst. For example, some embodiments use a Burst Stimulation ON watchdog timer to ensure that a time from a Burst Start Interrupt to a Burst Stop Interrupt is less than a defined maximum Burst Stimulation ON time for a neurostimulation burst. Some embodiments use a Burst Stimulation OFF watchdog timer to ensure that a time from a Burst Stop interrupt to a Burst Start Interrupt is more than a defined minimum Burst Stimulation OFF time between successive neurostimulation bursts. Some embodiments use both a Burst Stimulation ON watchdog time and a Burst Stimulation OFF watchdog timer.

Some embodiments are configured to look for a Burst Stop Interrupt during a Stop Interrupt Window. For example, if a prescribed neurostimulation dose includes a train or burst of neurostimulation of 10 seconds, then the Burst Stop Interrupt Window may be, by way of example and not limitation, 9 to 11 seconds after the neurostimulation burst was initiated. In some embodiments, the hardware enables a Burst Start interrupt only during the Burst Stimulation OFF period, in some embodiments, the hardware enables a Burst Stop Interrupt only during a Burst Stimulation ON period.

Some embodiments may include a counter to allow a limited number of pulses during the OFF period, and may reset the counter when the next ON period starts. A fault may be declared if a neurostimulation pulse is issued during the stimulation OFF period. Some embodiments count the neurostimulation pulses issued during the stimulation OFF period and declare a fault after a defined number of pulses are issued during the stimulation OFF period.

Some embodiments include firmware configured to look for a Burst Start Interrupt during a Start Interrupt Window. For example, if a prescribed neurostimulation dose includes a stimulation OFF time of 50 seconds between neurostimulation bursts, then the Start Interrupt Window may be, by way of example and not limitation, 45-55 seconds after the previous neurostimulation burst was stopped.

Figure 4A:
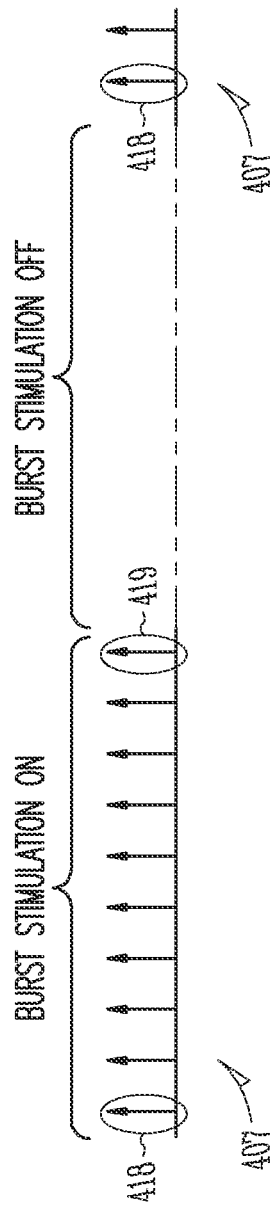
FIGS. 4A and 4B illustrate, by way of example, a function of a Stimulation ON watchdog timer, according to various embodiments.
Figure 4B:
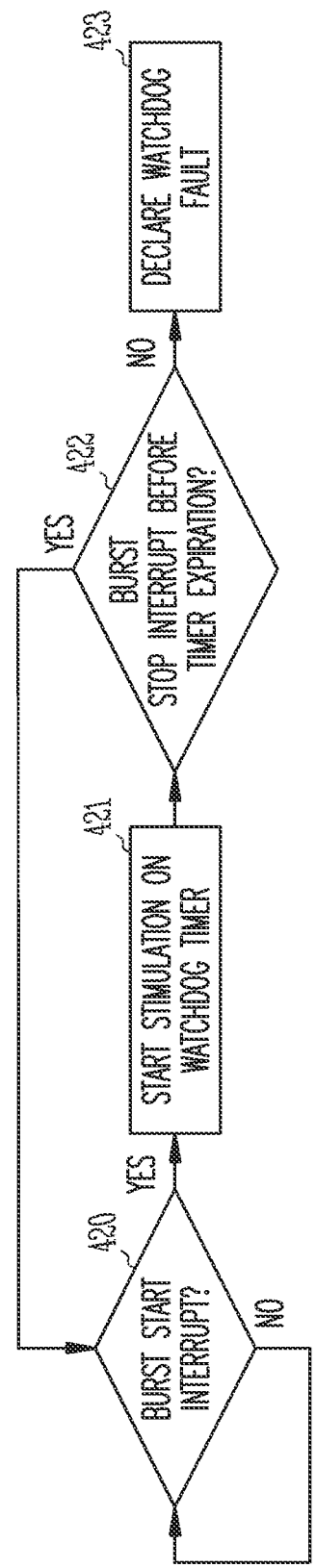

FIGS. 4A and 4B illustrate, by way of example, a function of a Stimulation ON watchdog timer, according to various embodiments. FIG. 4A illustrates neurostimulation bursts 407, which may be bursts of monophasic or biphasic pulses. The hardware state machine issues a Burst Start Interrupt 418 to the firmware of the processor for the first pulse in the burst 407, and issues a Burst Stop Interrupt 419 to the firmware of the processor for the last pulse in the burst 407. An embodiment of a Stimulation ON watchdog timer may be implemented using firmware in the processor and may wait for the Burst Start Interrupt at 420, and start the Stimulation ON watchdog tinier, as illustrated at 421, when the Burst Start Interrupt is received. The Stimulation ON watchdog timer waits for Burst Stop Interrupt at 422, returning to 420 if the Burst Stop Interrupt is received before the expiration of the Stimulation ON watchdog timer. If the Stimulation ON timer does not expire before the Burst Stop Interrupt is received, indicating that the burst duration is longer than a maximum Burst On time, then some embodiments may declare a watchdog fault at 423. Some embodiments may include a counter that counts the number of times that the Stimulation ON timer does not expire before the Burst Stop Interrupt is received, and declare a fault when the count reaches a defined threshold.

Figure 5A:
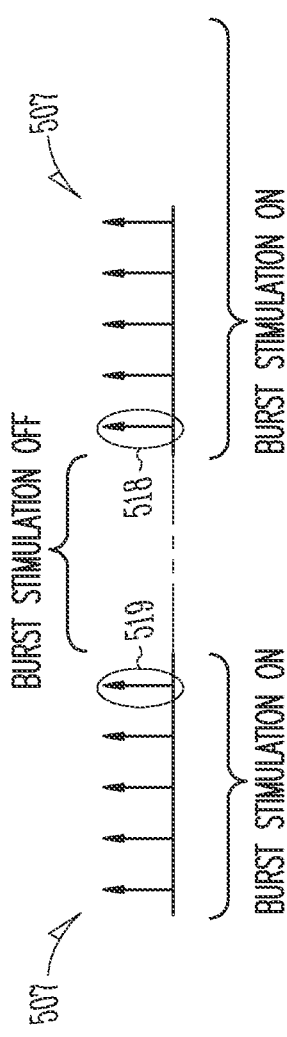
FIGS. 5A and 5B illustrate, by way of example, a function of a Stimulation OFF watchdog timer, according to various embodiments.
Figure 5B:
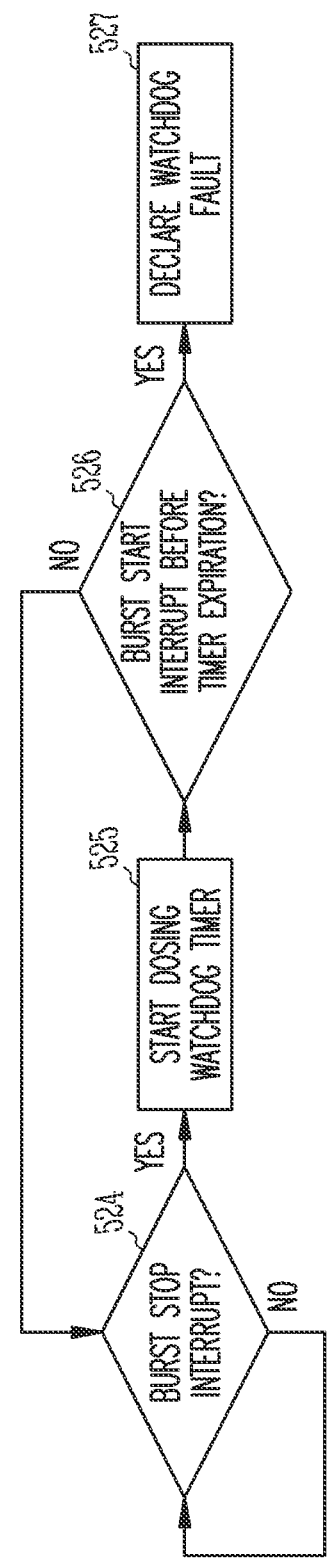

FIGS. 5A and 5B illustrate, by way of example, a function of a Stimulation OFF watchdog timer, according to various embodiments. FIG. 4A illustrates neurostimulation bursts 507. The hardware state machine issues a Burst Start Interrupt 518 to the firmware of the processor for the first pulse in the burst 507, and issues a Burst Stop Interrupt 519 to the firmware of the processor for the last pulse in the burst 507. An embodiment of a Stimulation OFF watchdog timer may be implemented using firmware in the processor and may wait for the Burst Stop Interrupt at 524, and start the Stimulation OFF watchdog timer, as illustrated at 525, when the Burst Stop Interrupt is received. The Stimulation OFF watchdog timer waits for Burst Start Interrupt at 526, returning to 525 if the Burst Start Interrupt is not received before the expiration of the Stimulation OFF watchdog timer. If the Burst Start Interrupt is received before the expiration of the Stimulation OFF watchdog timer, indicating that the burst stimulation off duration is shorter than a minimum Burst Stimulation OFF time, then some embodiments may declare a watchdog fault at 527. Some embodiments may include a counter that counts the number of times that the Burst Start Interrupt is received before the Stimulation OFF timer expires, and declare a fault when the count reaches a defined threshold.

Figure 6A:
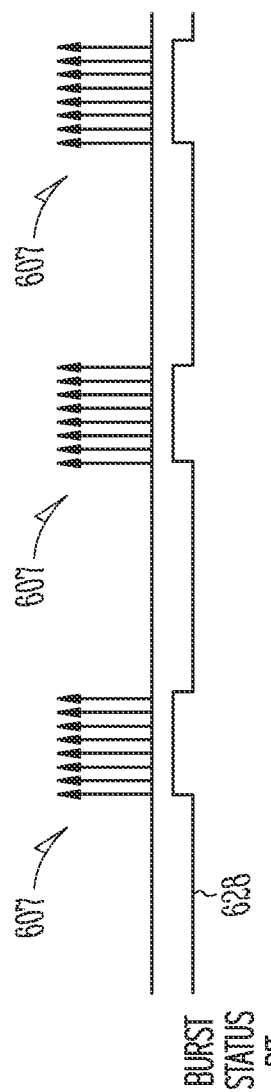
FIGS. 6A-6C illustrate, by way of example, a function of firmware operated on by the processor to monitor the neurostimulation using a burst status bit from the hardware statement machine.
Figure 6B:
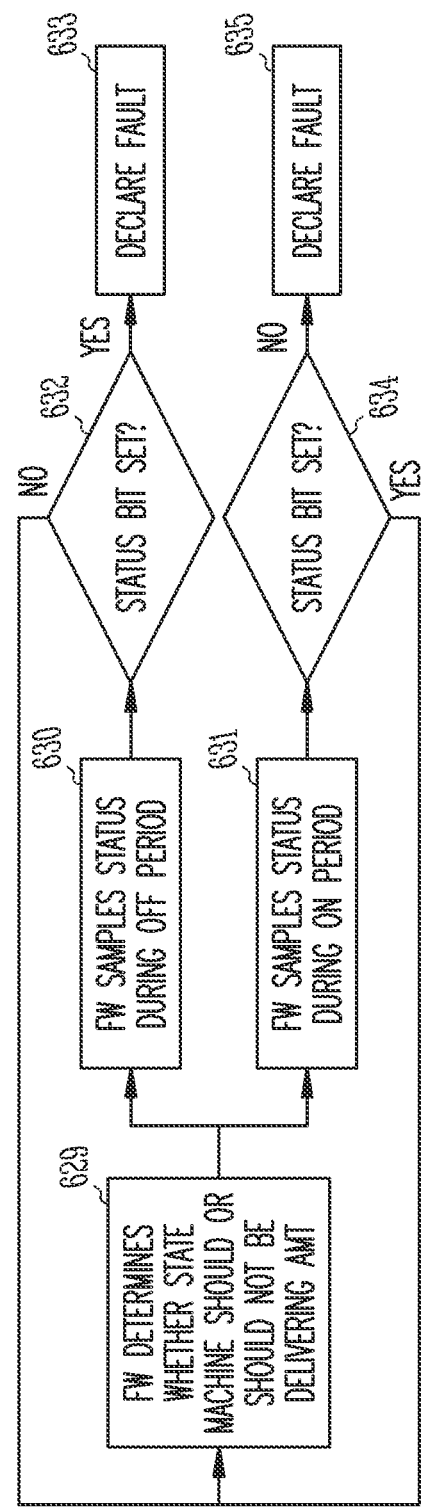
Figure 6C:
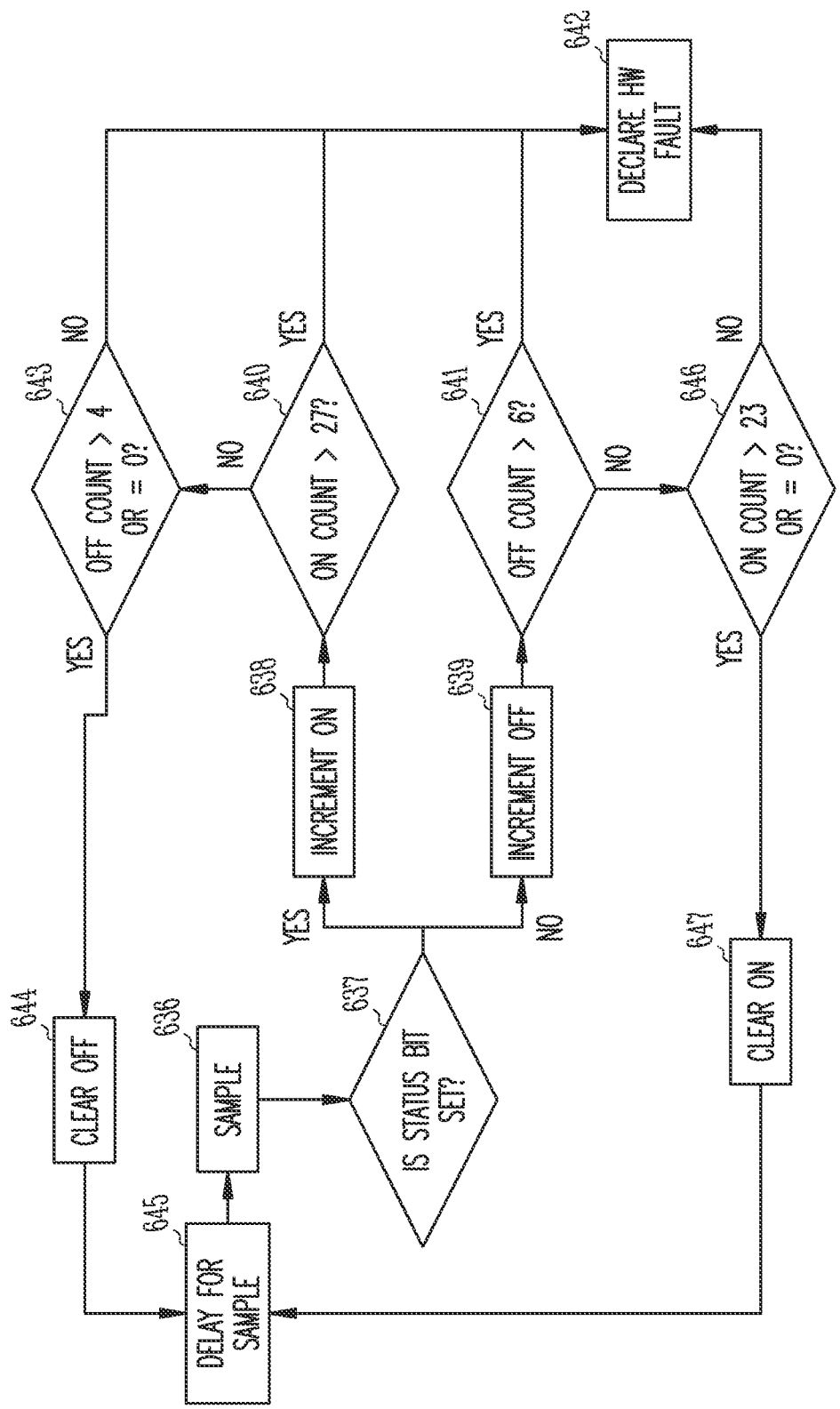

With reference to FIG. 3, the hardware state machine 311 may issue status information 317, rather than or in addition to interrupts. FIGS. 6A-6C illustrate, by way of example, a function of firmware operated on by the processor to monitor the neurostimulation using a burst status bit 628 from the hardware statement machine. FIG. 6A illustrates neurostimulation bursts 607, and further indicates an example of a status bit that toggles between a set state and a clear or not set state with the delivery of the bursts. In the illustrated example, the bit is set during the burst and is cleared during times between bursts. Some embodiments may alternatively clear the bit during the burst and set the bit during times between bursts.

FIG. 6B illustrates, by way of example, a process that may be implemented by the processor firmware to monitor the delivered neurostimulation. At 629, the firmware initiates a process to determine whether the state machine should or should not be delivering the neurostimulation. In performing this process, the firmware samples the burst status bit during Burst Stimulation OFF periods 630 and samples the burst status bit during Burst Stimulation ON periods 631. The processor controls the Burst Stimulation ON and OFF periods by using the AMT code to write data into the registers of the hardware state machine. The firmware cooperates with this AMT code to determine the Burst Stimulation ON and OFF times. The firmware proceeds to determine if the state of the status bit is as expected for times. For example, if a stimulation bit indicates that the hardware is delivering a burst, then the firmware may verify that the stimulation bit is not set at 632 for Burst Stimulation OFF periods 630, declaring a fault at 633 if the bit is set at 632, and the firmware may verify that the stimulation bit is set at 634 for Burst Stimulation ON periods 631, declaring a fault at 635 if the stimulation bit is not set at 634.

FIG. 6C illustrates, by way of example, a process that may be implemented by the processor firmware to monitor the delivered neurostimulation using periodic samples. By way of example and not limitation, the firmware may be configured to sample the status bit every two seconds, and the AMT code in the processor may be configured to deliver intermittent neurostimulation with 10 second Burst Stimulation ON times and 50 second Burst Stimulation OFF times between successive bursts. Other sampling times and other intermittent stimulation protocols may be used. In this example, one may expect that the hardware is delivering a stimulation burst for 5±1 consecutive samples, and may further indicate that the hardware is not delivering a stimulation burst for 25±2 consecutive samples. The sampling error or tolerance may be adjusted according to what is deemed appropriate for the prescribed therapy dose. At 636, the firmware samples the status bit from the hardware state machine. At 637, the firmware determines the state of the status bit (e.g. set or not set) to determine if the hardware state machine is delivering burst stimulation (ON) or not delivering burst stimulation (OFF). If burst stimulation is ON, then the firmware increments an ON counter at 638, and if the burst stimulation is OFF, then the firmware increments an OFF counter at 639. At 640, it is determined whether the ON count is greater than an ON threshold and an ON tolerance. For the 10 second ON 50 second OFF example identified above, the firmware may determine if the ON count is greater than 27. At 641, it is determined whether the OFF count is greater than an OFF threshold and an OFF tolerance. For the 10 second ON 50 second OFF example identified above, the firmware may determine if the OFF count is greater than 6. A hardware fault can be declared, as illustrated at 642, if either count is greater than its threshold and tolerance. At 643, it is determined whether the OFF count is greater than an OFF threshold less an OFF tolerance. For the 10 second ON 50 second OFF example identified above, the firmware may determine if the OFF count is greater than 4 or equal to 0. If not, the fault can be declared 642. If the OFF count is greater than 4 or equal to 0, the OFF count can be cleared 644. After a sampling delay 645, the next sample 636 of the status bit may be taken. At 646, it is determined whether the ON count is greater than an ON threshold less an ON tolerance or if the ON count equals 0. For the 10 second ON 50 second OFF example identified above, the firmware may determine if the ON count is greater than 23 or equal to 0. If not, the fault can be declared 642. If the ON count is greater than 23 or equal to 0, the ON count can be cleared 647. After a sampling delay 645, the next sample 636 of the status bit may be taken.

Figure 7:
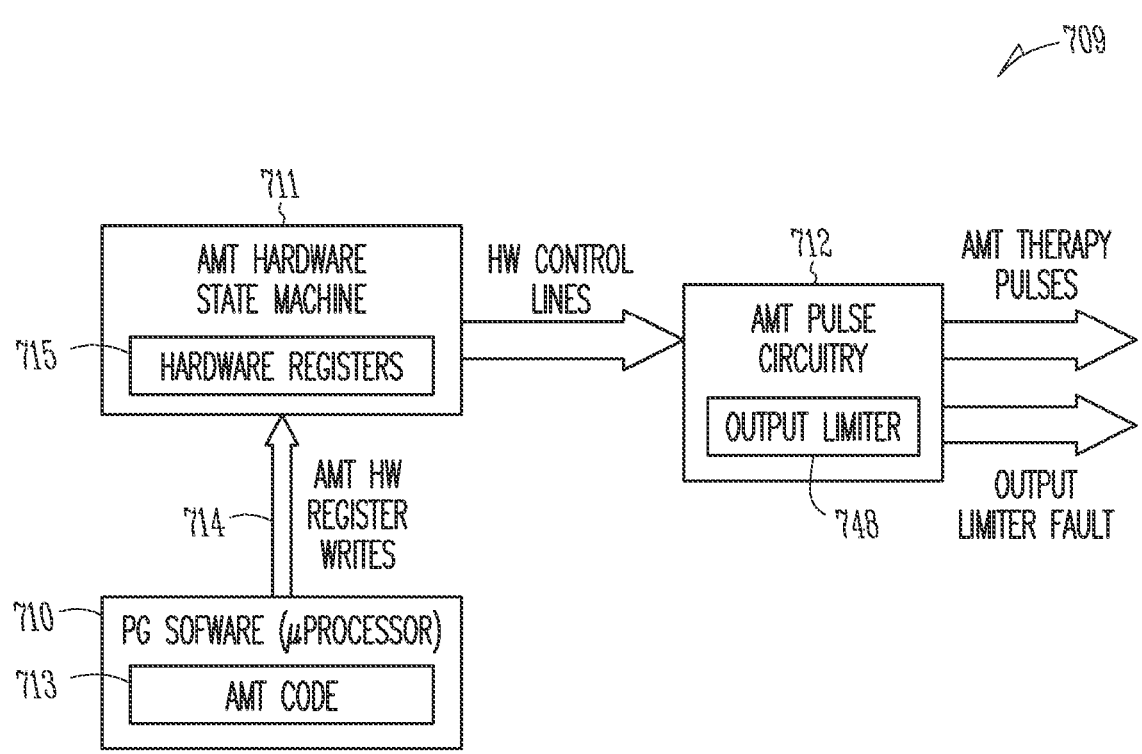
FIG. 7 illustrates, by way of example, an embodiment of a neural stimulator configured to monitor neurostimulation pulse frequency.

FIG. 7 illustrates, by way of example, an embodiment of a neural stimulator configured to monitor neurostimulation pulse frequency. The illustrated neural stimulator 709 includes a processor 710, a hardware state machine 711, and pulse circuitry 712. The processor is configured to operate on software, including pulse generator (PG) software used to control the delivery of the neurostimulation pulses. The PG software includes code 713 that provides instructions for delivering AMT. The processor may use the AMT code 713 to write data 714 into hardware registers 715 for the hardware state machine 711, and the hardware state machine 711 may use this data in the hardware registers to control the pulse circuitry 712 to output a train of pulses for the AMT. The pulse circuitry 712 may include an output limiter 748. The output limiter 748 may be used in addition to or as an alternative to the watchdog functions illustrated in FIGS. 3-6. The output limiter 784 may be a programmable output frequency output limiter used to avoid excessive charge delivery caused by excessive pulse frequencies.

Potential causes of excessive pulse frequencies may include a corrupted or incorrectly programmed hardware frequency register or if clocks are operating too fast, or if there are race conditions or other hardware failure modes.

Figure 8A:
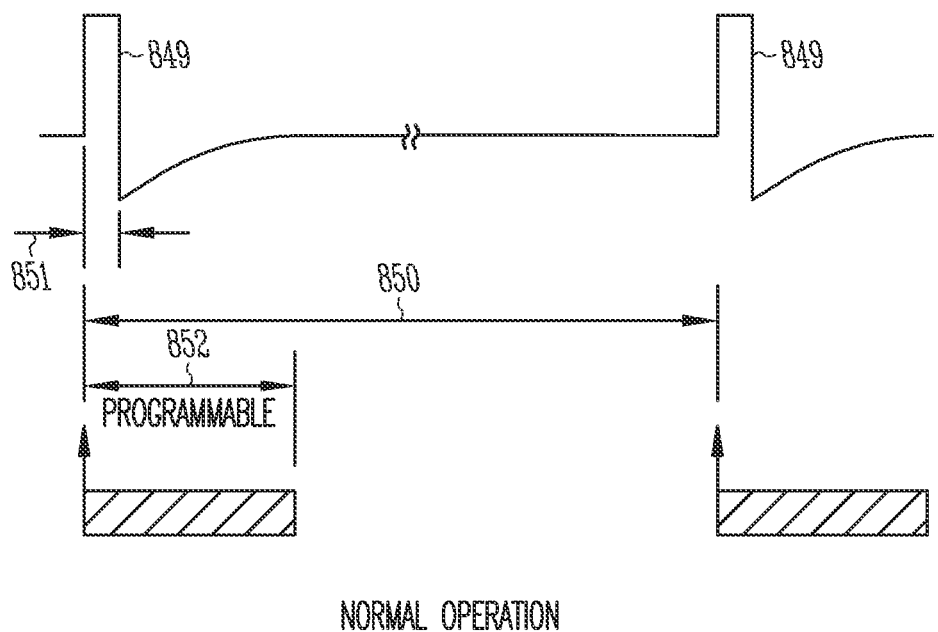
FIGS. 8A-8B illustrate, by way of example and not limitation, an implementation of an output limiter embodiment.
Figure 8B:
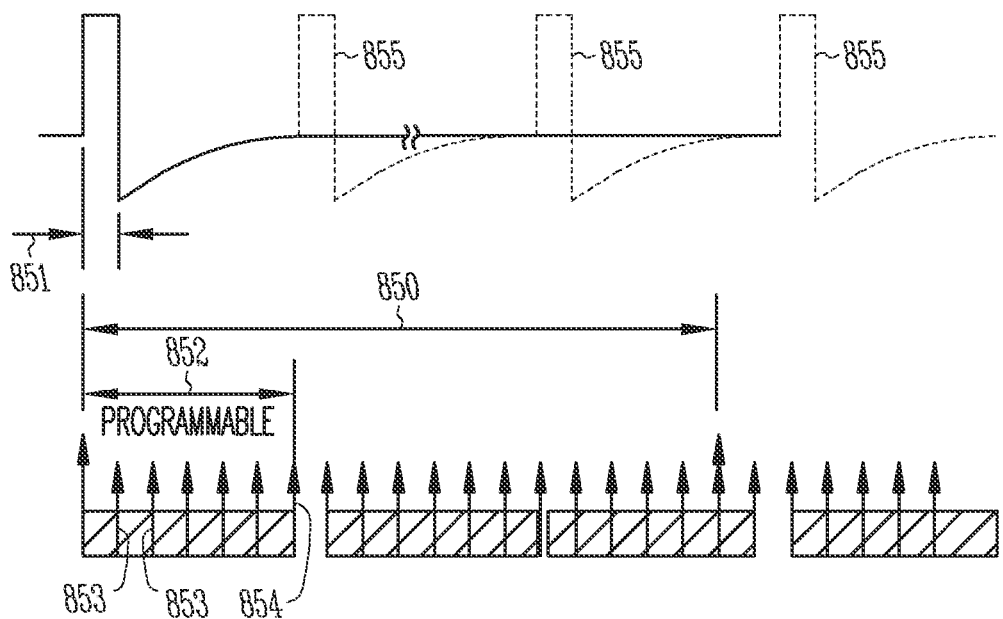

Various embodiments may use a period after a neurostimulation pulse, within a burst of pulses, during which time subsequent pulses are blocked from issuing. This period may be a programmable period. FIGS. 8A-8B illustrate, by way of example and not limitation, an implementation of an output limiter embodiment. FIG. 8A is an example of normal operation where the pulses 849 are being delivered at an appropriate pulse frequency (a normal pulse interval 850 between successive pulses). The purses have a pulse width 851. The output limiter provides a programmable window 852 for blocking subsequent pulses that may occur to fast. In the illustrated normal operation, the programmable window does not block the next pulse if it occurs at the expected time. FIG. 8B is an example of a stimulator attempting to deliver subsequent neurostimulation pulses 853 too quick after an initial pulse. A pulse 854 is allowed after the programmable window 852, at which time another pulse window is initiated. Thus, although the subsequently delivered neurostimulation pulses 855 are delivered more quickly than the normal pulse interval 850, it is significantly less than if all attempted pulses were actually delivered. This limit on the purse frequency provides a limit on the charge delivered to the neural target. The duration of the window 852 may be appropriately determined for the prescribed neurostimulation therapy. The programmable blocking period provides flexibility for upper frequency rate limiting. A fault may be declared when the hardware blocks a pulse or a defined number of pulses in a defined period of time.

Figure 9A:
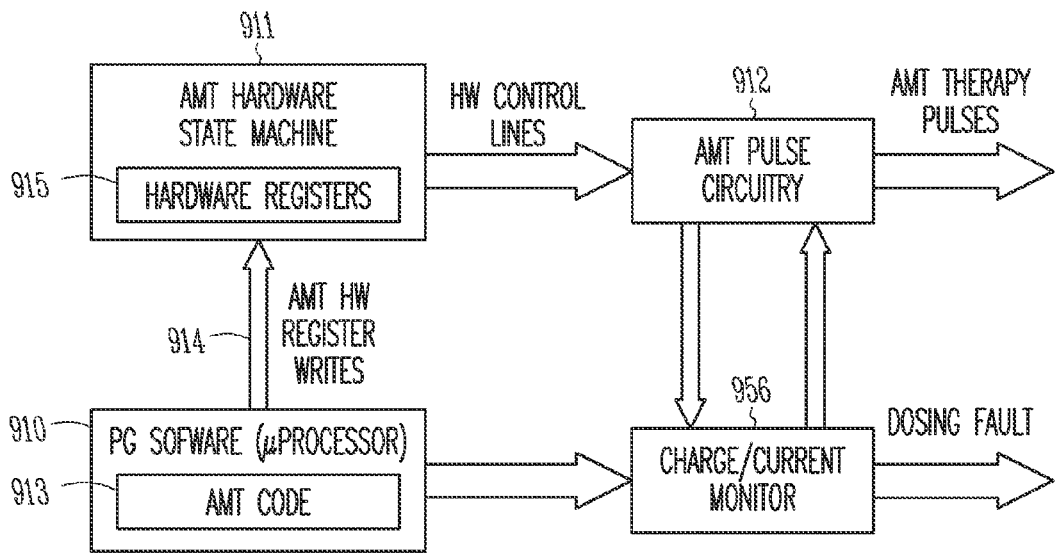
FIGS. 9A-C illustrate, by way of example, an embodiment of a neural stimulator configured to monitor neurostimulation charge.
Figure 9B:
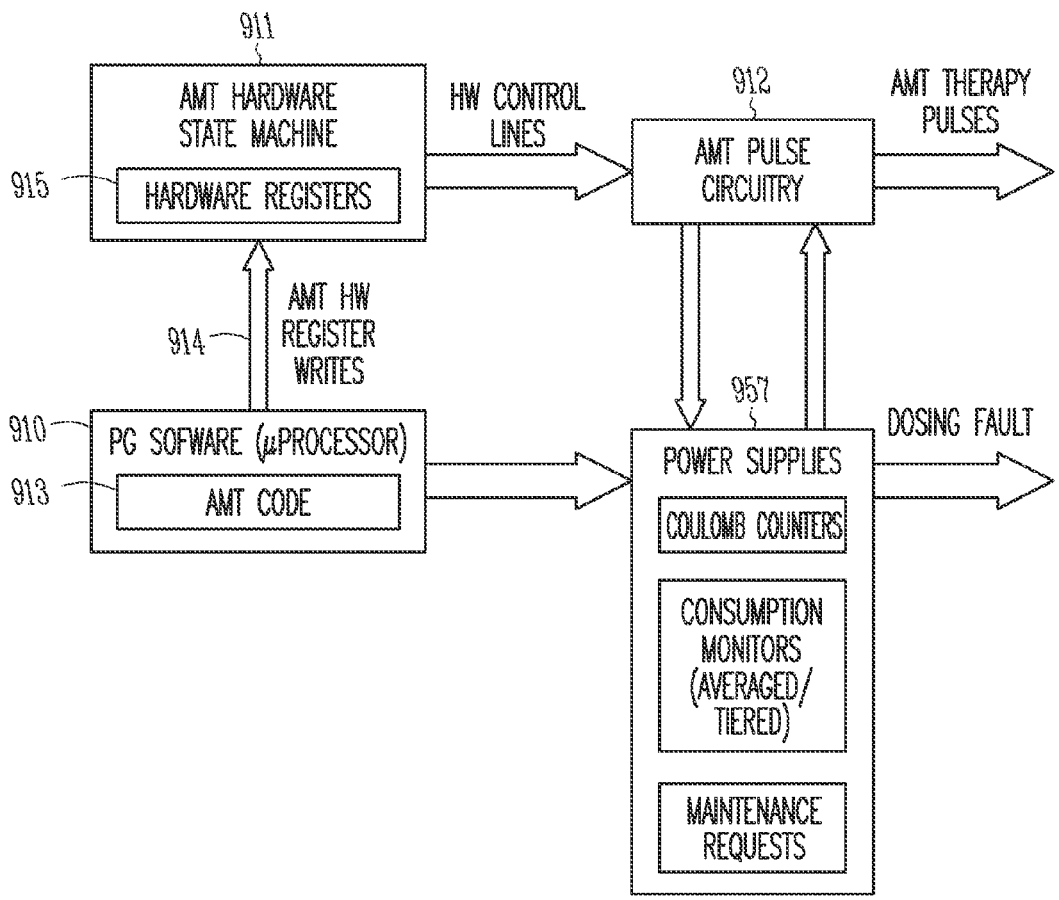
Figure 9C:
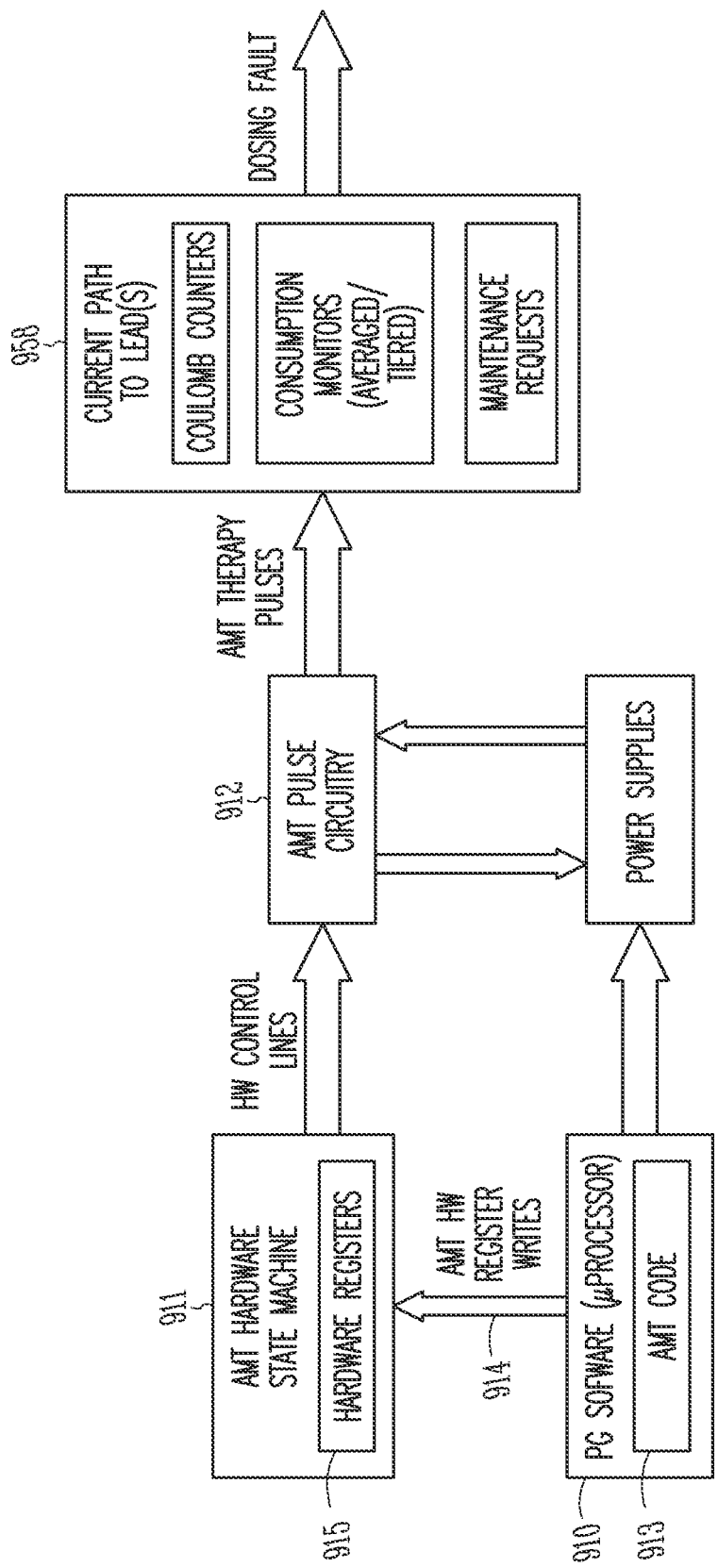

FIGS. 9A-C illustrate, by way of example, an embodiment of a neural stimulator configured to monitor neurostimulation charge. The illustrated neural stimulator includes a processor 910, a hardware state machine 911, and pulse circuitry 912. The processor is configured to operate on software, including pulse generator (PG) software used to control the delivery of the neurostimulation pulses. The PG software includes code 913 that provides instructions for delivering the autonomic modulation therapy (AMT). The processor may use the AMT code 913 to write data 914 into hardware registers 915 for the hardware state machine 911, and the hardware state machine 911 may use this data in the hardware registers to control the pulse circuitry 912 to output a train of pulses for the AMT. The neural stimulator may include a monitor of charge or current 956, which may be used in addition to or as an alternative to the watchdog functions illustrated in FIGS. 3-6 and/or the output limiter illustrated in FIGS. 7 and 8A-8B. In some embodiments, the charge/current monitor 956 may use measures of current consumption to verify that the delivered charge is within constraints for the prescribed neurostimulation therapy.

In some embodiments, the charge/current monitor may be implemented within a power supply to measure the charge depletion from a power supply 957, such as illustrated in FIG. 9B by way of example. With some knowledge of the power consumption required to operate the neural stimulator, the measure of charge depletion from the power supply can be used to estimate the amount of charge delivered into tissue. For example, the measure may compensate or otherwise account for background current draw or extraneous current draws such as telemetry. This may be omitted in providing a desired level of accuracy if the charge consumed in delivering neurostimulation to the tissue is much greater than the charge consumed for other device functions.

In some embodiments, the charge/current monitor may be implemented to monitor charge or current flowing through a current path to the neurostimulation lead(s) 958, such as illustrated in FIG. 9C by way of example, which may provide more accuracy as it does not require an estimate of the power consumption required to operate the neural stimulator.

In some embodiments, the charge/current monitor provides an estimate of charge delivered to the tissue based on the number of times that the power supply required "maintenance" or "service" to keep the supply at a programmed level. A measurement may be made, such as may be made in the lab by the design engineer, to determine how much charge is provided to the power supply per maintenance event. This value and the number of maintenance events can be used to estimate a consumed charge over a time period. This "per maintenance event" value could be a calibration constant, varying device to device, or it could be a constant for all devices of the same design.

In some embodiments, the charge/current monitor may count the number of pulses, or burst of pulses delivered over a time period or periods to provide an estimate of the charge delivered to the neural tissue. Accuracy may be improved with safeguards implemented to maintain the desired amplitude of the neurostimulation signal and pulse width of the neurostimulation signal.

Figure 10:
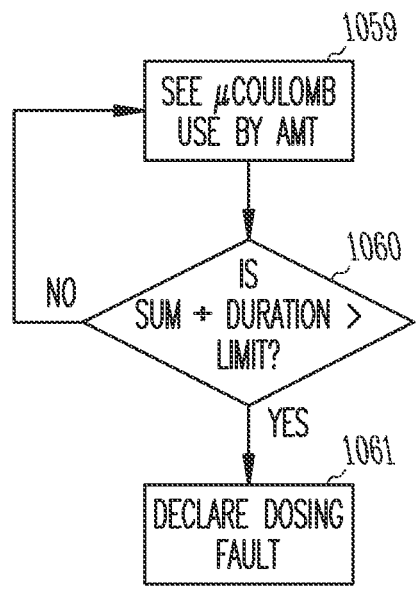
FIG. 10 illustrates, by way of example and not limitation, an embodiment of a coulomb counter.

FIG. 10 illustrates, by way of example and not limitation, an embodiment of a coulomb counter. At 1059, the coulombs used in delivering the neurostimulation are counted. These coulombs may be based on the charge depleted from the power supply as illustrated in FIG. 9B or may be based on the charge delivered through the lead for stimulation of the neural target. The coulomb counter continues to count and sum the counted coulombs until the coulombs counted for a period of time exceeds a defined threshold at which time a fault may be declared. For example, as illustrated at 1060, the coulomb sum may be divided by the duration, thus providing a measure of an average current for that duration, which can be compared to the limit or threshold. If the average current is greater than the threshold, then a fault 1061 can be declared.

Figure 11:
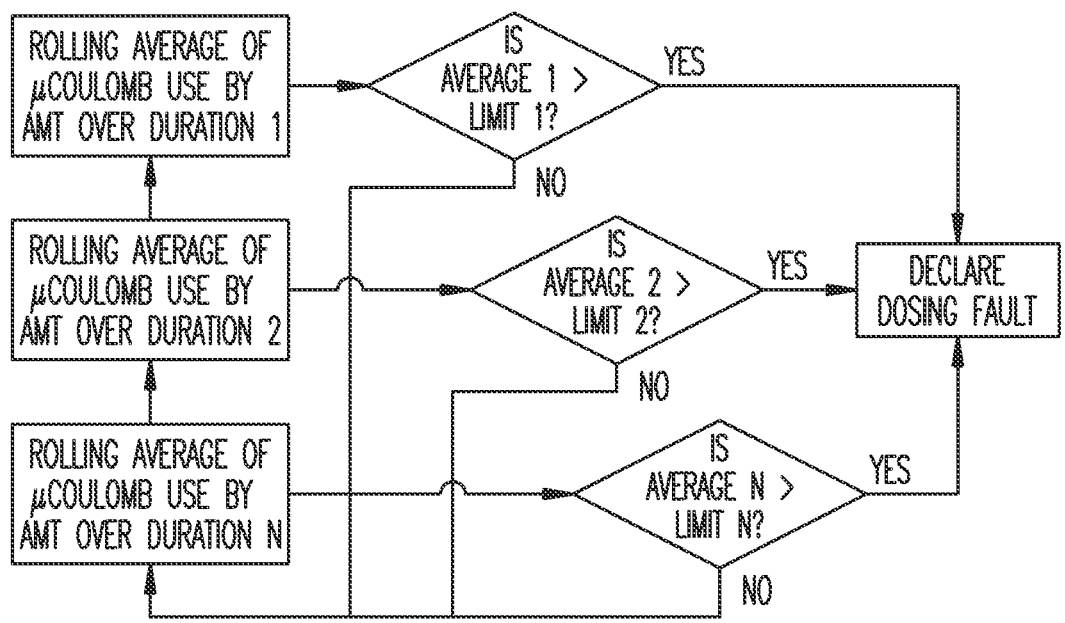
FIG. 11 illustrates, by way of example and not limitation, an embodiment of a coulomb counter that implements a rolling average and a tiered threshold levels used to declare a fault.

FIG. 11 illustrates, by way of example and not limitation, an embodiment of a coulomb counter that implements a rolling average and a tiered threshold levels used to declare a fault. The average coulomb use over a time duration may be implemented similar to steps 1059 and 1060 in FIG. 10. The different durations represent different lengths of time. For example, duration 1 may be a relatively short period of time over which a rotting average of charge use is determined, duration 2 may be a longer period over which a rolling average of charge use is determined, and duration N may be an even longer period of time over which a rolling average of charge use is determined. The number of tiers may be 2, 3 or more tiers. A tier may average coulomb use over a duration of time varying from on the order of a second or seconds, or on the order of a minute or minutes, or on the order of an hour or hours, or on the order of a day or days, or on the order of a week or weeks, or on the order of a month, or months or even years for chronically delivered neurostimulation therapies such as AMT for hypertension or heart failure. This tiered approach recognizes that the safety and/or the efficacy of a delivered neurostimulation dose may be affected by relatively short stimulation time, and may be affected by the cumulative effect of the delivered charge over longer periods of time. In some embodiments, the thresholds or limits used for the tiers may depend on the neurostimulation electrode area, as charge density (current× area) is a factor in damaging neural tissue.

The monitoring of the charge/current consumption also protects against failures (hardware race conditions, inappropriate firmware loops, clock deviations, corrupted hardware registers, improperly trimmed outputs, etc.). The charge monitoring may continue even if a fault is declared.

Figure 12:
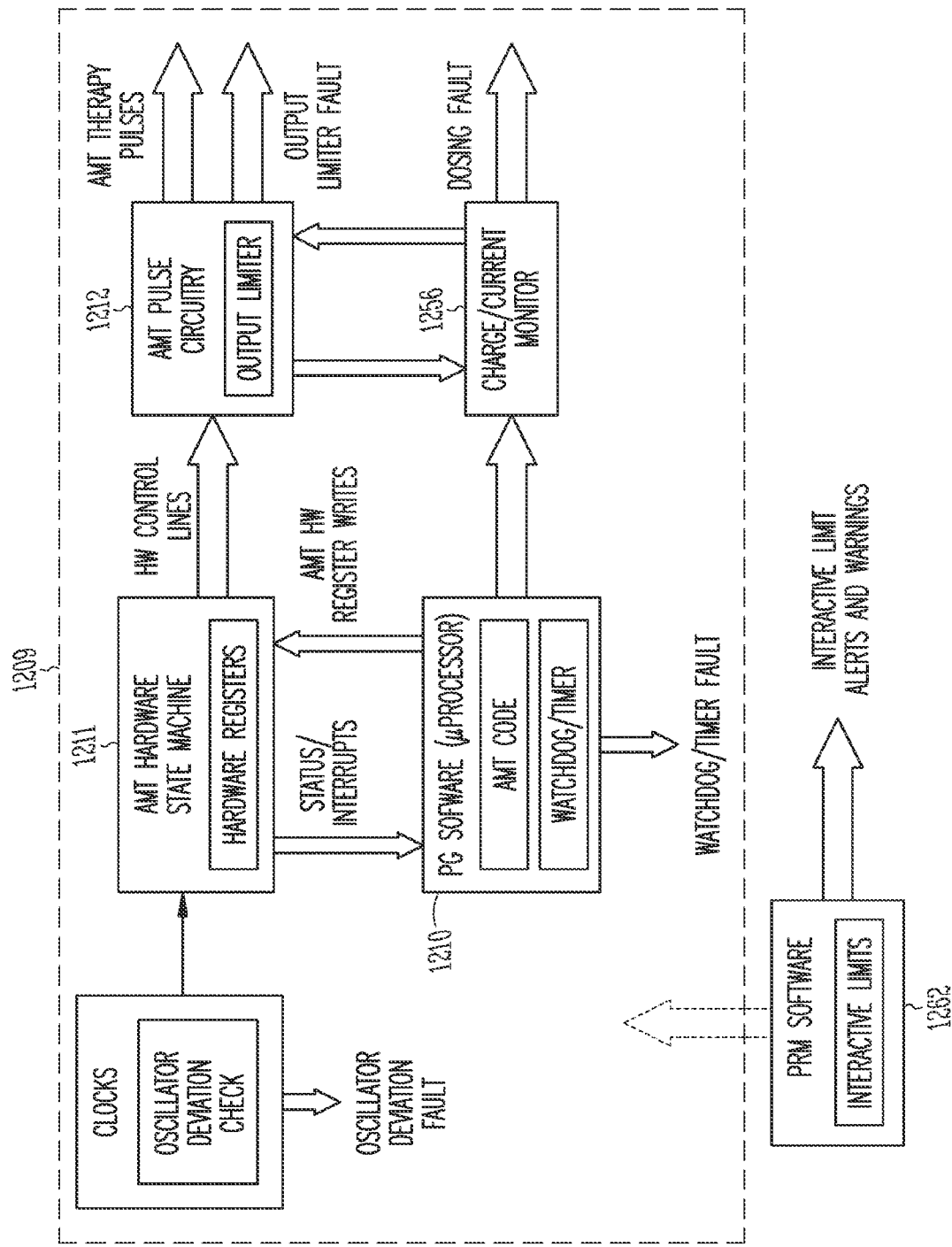
FIG. 12 illustrates, by way of example, an embodiment of a neurostimulation system that includes a neural stimulator and a programmer.
Figure 13:
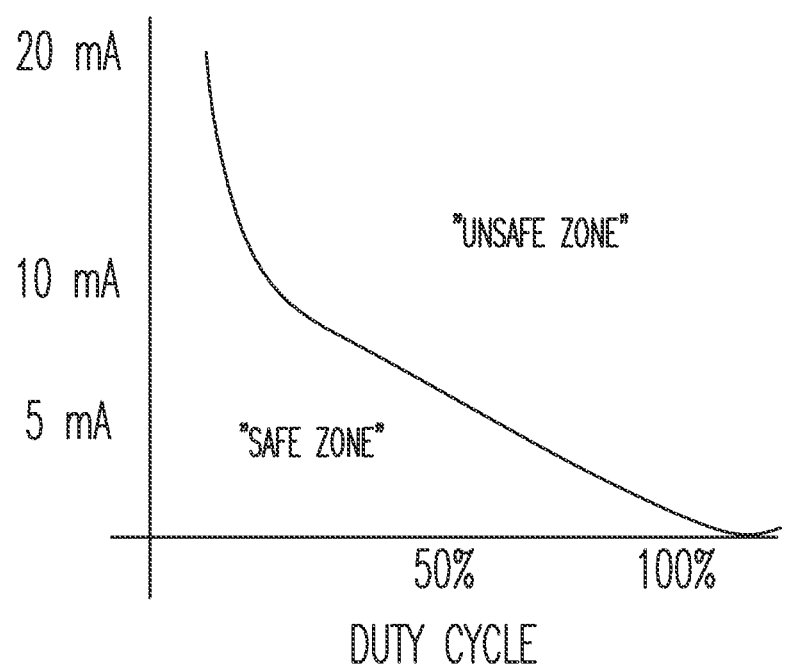
FIG. 13 provides, by way of example, an illustration of the parameter interaction of duty cycle and pulse amplitude in defining safe and unsafe stimulation zones.

FIG. 12 illustrates, by way of example, an embodiment of a neurostimulation system that includes a neural stimulator 1209 and a programmer 1262. The illustrated neural stimulator includes a processor 1210, a hardware state machine 1211, pulse circuitry 1212, and monitor of charge or current 1256. Any one or various combinations of the techniques for monitoring neurostimulation dose may be included in the neural stimulator. The neural stimulator may be configured to perform oscillator deviation checks on clock(s) used by the neural stimulator as yet another safeguard to verify the neurostimulation dose. Some embodiments may declare an oscillator deviation fault if the oscillator deviation check fails. The programmer 1262 may be configured with parameter interaction limits, which allows only certain combinations of stimulation parameters such as may be beneficial to ensure safe neurostimulation delivery. FIG. 13 provides, by way of example, an illustration of the parameter interaction of duty cycle and pulse amplitude in defining safe and unsafe stimulation zones. Similarly, an allowed therapy zone for a prescribed dose of neurostimulation therapy may be defined using the interaction between two or more parameters.

To add an additional robustness for the monitoring of neurostimulation doses, some embodiments of the neural stimulator may be implemented using more than one integrated circuit. For example, the hardware state machine may be implemented in an integrated circuit and the processor may be implemented using another integrated circuit. Such use of separate integrated circuits provides additional isolation and protection from problems with the circuitry. With the additional isolation and protection provided by the use of separate integrated circuits, the various techniques for monitoring the delivered dose, such as for safety or for dose verification purposes, can provide assurance that the desired dose of neurostimulation is being delivered.

Neurostimulation may be delivered in a manner that stimulates neural activity in the target nerve or in a manner that inhibits or blocks neural activity in the target nerve. The present subject matter is applicable to either stimulation or inhibition.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable medical device, comprising:
a neural stimulator configured to deliver a neurostimulation therapy with a neural stimulation pulse frequency, wherein a dose of the neurostimulation therapy is provided by a number of neurostimulation pulses over a period of time, wherein the neural stimulator includes a clock with an oscillator, a hardware state machine operationally connected to the clock to provide pulse timing control signals, and pulse circuitry configured to receive the timing control signals and deliver neurostimulation pulses with a pulse frequency controlled using the timing control signals, the pulse circuitry including a frequency output limiter configured to avoid excessive charge delivery, wherein the frequency output limiter is configured to block a pulse from being issued only for a limited period of time after a preceding pulse, and thereby allow a subsequent pulse after the limited period of time.

2. The device of claim 1, wherein the limited period of time is a programmable period of time.

3. The device of claim 1, wherein the device is configured to declare a fault when a defined number of pulses are blocked by the frequency output limiter, the defined number of pulses being one or more pulses.

4. The device of claim 1, wherein the device includes a charge consumption monitor, and declares a fault if the charge consumption is not within the dosing parameters.

5. The device of claim 4, further comprising a power supply, wherein the charge consumption monitor is configured to measure charge depletion from the power supply.

6. The device of claim 4, wherein the neural stimulator is configured to deliver neurostimulation pulses through at least one lead, and the charge consumption monitor is configured to monitor charge or current flow to the at least one lead.

7. The device of claim 4, wherein the charge consumption monitor includes a coulomb counter.

8. The device of claim 4, wherein the charge consumption monitor is configured to implement a rolling average and tiered threshold levels to declare the fault.

9. The device of claim 4, wherein the device is configured to perform a device action in response to the fault, wherein the device action includes stopping or altering the neurostimulation therapy in response to the fault.

10. A method, comprising:
delivering a neurostimulation therapy with a neural stimulation pulse frequency, wherein a dose of the neurostimulation therapy is provided by a number of neurostimulation pulses over a period of time, wherein delivering the neural stimulation therapy includes providing pulse timing control signals using a clock with an oscillator and a hardware state machine operationally connected to the clock, and further includes using pulse circuitry to receive the timing control signals and deliver neurostimulation pulses with a pulse frequency controlled using the timing control signals and using a frequency output limiter to avoid excessive charge delivery, wherein using the frequency output limiter to avoid excessive charge delivery includes using the frequency output limiter to block a pulse from being issued only for a limited period of time after a preceding pulse, and thereby allow a subsequent pulse after the limited period of time.

11. The method of claim 10, wherein the limited period of time is a programmable period of time, and using the frequency output limiter to avoid excessive charge delivery includes using a programmable frequency output limiter to block a pulse from being issued for the programmable period of time after a preceding pulse.

12. The method of claim 10, further comprising declaring a fault when a defined number of pulses are blocked by the frequency output limiter, the defined number of pulses being one or more pulses.

13. The method of claim 10, further comprising monitoring charge consumption and declaring a fault if the charge consumption is not within the dosing parameters.

14. The method of claim 13, wherein monitoring charge consumption includes measuring charge depletion from the power supply.

15. The method of claim 13, wherein monitoring charge consumption includes monitoring charge or current flow to at least one lead.

16. The method of claim 13, wherein monitoring charge consumption includes using a coulomb counter to monitor charge consumption.

17. The method of claim 13, wherein monitoring charge consumption includes using a rolling average of coulomb use and tiered threshold levels to declare the fault.

18. The method of claim 13, further comprising stopping or altering the neurostimulation therapy in response to the fault.

* * * * *